(12) United States Patent
Edmonson et al.

(10) Patent No.: US 7,451,649 B2
(45) Date of Patent: Nov. 18, 2008

(54) DIFFERENTIATION AND IDENTIFICATION OF ANALOGOUS CHEMICAL OR BIOLOGICAL SUBSTANCES WITH BIOSENSORS

(75) Inventors: Peter J. Edmonson, Hamilton (CA); William D. Hunt, Decatur, GA (US); Desmond D. Stubbs, Riverdale, GA (US); Sang Hun Lee, Duluth, GA (US)

(73) Assignee: P.J. Edmonson Ltd., Hamilton, Ontario (CA)

( * ) Notice: Subject to any disclaimer, the term of this patent is extended or adjusted under 35 U.S.C. 154(b) by 330 days.

(21) Appl. No.: 11/088,809

(22) Filed: Mar. 25, 2005

(65) Prior Publication Data

US 2006/0213271 A1 Sep. 28, 2006

(51) Int. Cl.
*H01L 41/00* (2006.01)
*G01N 9/24* (2006.01)
*G01N 29/00* (2006.01)

(52) U.S. Cl. .................................... 73/599; 310/313 D
(58) Field of Classification Search .................. 73/599, 73/584; 310/313 D
See application file for complete search history.

(56) References Cited

U.S. PATENT DOCUMENTS

| | | | |
|---|---|---|---|
| 4,361,026 A * | 11/1982 | Muller et al. | 73/24.01 |
| 5,571,568 A * | 11/1996 | Ribi et al. | 427/487 |
| 6,848,295 B2 * | 2/2005 | Auner et al. | 73/24.06 |
| 6,967,428 B2 * | 11/2005 | Edmonson et al. | 310/313 D |
| 2003/0231107 A1 * | 12/2003 | Edmonson et al. | 340/10.42 |
| 2003/0233197 A1 * | 12/2003 | Padilla et al. | 702/20 |
| 2005/0116263 A1 * | 6/2005 | Lu et al. | 257/252 |
| 2006/0049714 A1 * | 3/2006 | Liu et al. | 310/313 R |

FOREIGN PATENT DOCUMENTS

WO    WO 2005001424 A2 *    1/2005

* cited by examiner

*Primary Examiner*—Hezron Williams
*Assistant Examiner*—Tamiko Bellamy
(74) *Attorney, Agent, or Firm*—Robert F. Delbridge (57) ABSTRACT

A biosensor detection system for detecting a particular substance has at least two biosensor devices. Each biosensor device includes a piezoelectric material, an input transducer mounted on the piezoelectric material to receive an input radio frequency signal and propagate a corresponding acoustic wave within the piezoelectric material and an output transducer mounted on the piezoelectric material to receive the acoustic wave and transmit a corresponding output radio frequency signal. A biolayer is mounted on the piezoelectric material to receive a substance to be tested and cause a corresponding change in the acoustic wave. An oscillator circuit is connected to the input transducer and to the output transducer, the oscillator circuit including an amplifier and providing an output signal indicative of a change in the acoustic wave. The biosensor devices having two different biolayers, whereby the output signals can be utilized to detect receipt of a particular substance by the biolayers of the biosensor devices.

10 Claims, 9 Drawing Sheets

Truth Table

| Mapped Binary Bits | 8-QAM Phasor Component | |
|---|---|---|
| | Amplitude | Phase |
| 0 0 0 | 0.50 | -135° |
| 0 0 1 | 1.25 | -135° |
| 0 1 0 | 0.50 | -45° |
| 0 1 1 | 1.25 | -45° |
| 1 0 0 | 0.50 | +135° |
| 1 0 1 | 1.25 | +135° |
| 1 1 0 | 0.50 | +45° |
| 1 1 1 | 1.25 | +45° |

TNT (trinitrotoluene)
610

RDX, C-4
(Cyclotrimethylene trinitramine)
620

Musk Oil, Musk Xylene
630

Ammonium Nitrate
640

Truth Table

| Substance Input | Mapped Regions |
|---|---|
| | Coordinates Range (Hz) |
| TNT | (-100 to -700) |
| RDX | (-1000, 1000) to (-2250, 2200) |
| C4 | (-600, 1600) to (-1750, 4600) |
| Musk Oil | (-10, -700) to (-1700, -1300) |
| Ammonium Nitrate | Clustered about coordinate (-1000, 1850) |

DIFFERENTIATION AND IDENTIFICATION OF ANALOGOUS CHEMICAL OR BIOLOGICAL SUBSTANCES WITH BIOSENSORS

FIELD OF INVENTION

This invention relates to differentiating and identifying analogous chemical or biological substances with biosensors.

BACKGROUND OF INVENTION

In general, biosensors are distinguished from chemical sensors in that they use a sensor layer of biological origin (for example an antibody, cell or enzyme) immobilized on a surface as the target-sensitive component of the sensor. Recent literature by Hunt et al., "Time dependent signatures of acoustic wave biosensors," *IEEE Proceedings*, Vol. 91, no. 6 pp. 890-901, June 2003 and Stubbs, D. D., Lee, S. H. and Hunt, W. D., "Investigation of cocaine plumes using surface acoustic wave immmunosassay sensors," *Analytical Chemistry*, vol. 75, no. 22, pp. 6231-6235, Nov. 15, 2003, has demonstrated that an acoustic wave biosensor with an immobilized biolayer need not be restricted to the detection of biomolecules within the liquid phase, but can detect low vapour pressure chemical molecules such as bacteria, cocaine and explosives.

The detection of such chemical or biological molecules has in the past involved the use of frequency offset versus time graphs. A simple oscillator circuit having an acoustic wave biosensor within its feedback path has its operating frequency altered in a manner depending on the binding events which take place between the antibody and the chemical or biological substance. The binding events change the mass loading and stiffness parameters of a piezoelectric crystal in the oscillator circuit, which subsequently alters the velocity of the propagating acoustic wave and therefore affects the oscillator feedback element. As a result, the frequency of the oscillator is changed.

An object of this invention is to reduce the mathematical complexity required with previous methods of differentiating and identifying analogous chemical or biological substances with surface acoustic wave biosensors.

SUMMARY OF INVENTION

According to the present invention, the mathematical complexity required for previous methods can be reduced by uniquely creating chemical or biological immunosensor detection methods from principles utilized in the field of digital radio.

The interaction of the high sensitivity and selectivity of an antibody/antigen binding event can be compared to that of a digital radio receiver. The receiving sensitivity of a radio indicates the level of signal strength which must be present to correctly receive data at a specified bit-error-rate (BER). The role of which type of modulation techniques which may be necessary to achieve the required BER must be considered. Frequency based modulation (FM) schemes exhibit an improved BER over amplitude modulation (AM) schemes. The detection scheme for the immunosensor utilizes a frequency based modulation scheme where the binding of specific substances on a biolayer results in a change in the frequency of the circuitry. Specific experiments were performed to measure the sensitivity of such a frequency-based immunosensor. The results yielded sensitivity readings of 20 Hz per picogram with a detection limit of a few picograms, (Stubbs, D. D., Lee, S. H. and Hunt, W. D., "Investigation of cocaine plumes using surface acoustic wave immunosassay sensors," *Analytical Chemistry*, vol. 75, no. 22, pp. 6231-6235, Nov. 15, 2003).

A second technique in the field of digital radio involves the definition of selectivity in a radio system and is often specified as the ability to remove out-of-band unwanted signals. Solutions with radio systems to achieve high selectivity usually involve hardware filters or software code residing in digital signal processors (DSPs). The specificity of the immobilized antibodies has inherently a high selectivity of desired binding molecules. Systems implementing immobilized antibodies within the biosensor hardware can relax the DSP requirements and still maintain a high degree of selectivity.

An injection oscillator can also be used. Both sensitivity and selectivity are further enhanced within an immunosensor by utilizing an acoustic wave oscillator which in actuality is an acoustic wave based neural network which can associate, categorize and store an input stimulus. An acoustic wave injected-locked oscillator neuron (ILON) has a high dynamic range, excellent sensitivity and an inherent narrow-band selectivity. Examples of a SAW based neural network which has previously been proposed by one of the inventors herein are illustrated in: P. J. Edmonson, P. M. Smith and C. K. Campbell, "Injection locked oscillators: Dynamic behaviour and applications to neural networks," *Proceedings* 1993 *IEEE Ultrasonics Symposium*, Baltimore, Md., pp. 131-135, October 1993.

The inherent selectivity, sensitivity and high dynamic range which can be built into both the electrical and biological hardware of a biosensor in accordance with the present invention greatly reduces the number of instructions and computational effort required for the differentiation and identification of chemical or biological substances. Therefore the present invention greatly reduces the necessity for complex mathematical computations, which will in turn result in lower powered devices which function longer on a battery and are lower in cost due to the reduced complexity of the circuit, such as a reduced bit and lower clock rate digital signal processors.

An important feature of this invention is the concept of semi-orthogonal signals. Within a code division multiple access (CDMA) digital radio communication system, the coded sequences are not truly orthogonal because such systems are inherently asynchronous between pairwise communicators. There is no coordination between the timing as to when two coded sequences code X and code Y would start and a degree of interference would occur between the coded sequence X and detector Y and coded sequence Y and detector X. Within a biosensor system, the concept of semi-orthogonal generated interference allows the ability of antibody X and antibody Y to cross react with multiple antigens. This phenomenon is known as the promiscuity of the antibodies. This conformational diversity allows related groups of substances to cross-react and bind with a certain level of affinity with the X antibody and the Y antibody. In many standard protocols, such as ELISA, only the antigens with very high affinity are still bound to the antibody at the end of the process of the protocol. By virtue of our real time analysis and the approach to chemical orthogonality in this invention, it is possible to discern gradations of affinity between a receptor molecule and its ligand.

According to one aspect of the present invention therefore, a biosensor detection system for detecting a particular substance has at least two biosensor devices, each biosensor device including a piezoelectric material, an input transducer mounted on the piezoelectric material to receive an input radio frequency signal and propagate a corresponding acoustic wave within the piezoelectric material, an output transducer mounted on the piezoelectric material to receive the acoustic wave and transmit a corresponding output radio frequency signal, a biolayer mounted on the piezoelectric material to receive a substance to be tested and cause a corresponding change in the acoustic wave, and an oscillator circuit connected to the input transducer and to the output transducer, said oscillator circuit including an amplifier and providing an output signal indicative of a change in the acoustic wave, the biosensor devices having two different biolayers, whereby the output signals can be utilized to detect receipt of a particular substance by the biolayers of the biosensor devices.

The biosensor detection system may include a signal state-space map formulator operable to produce a signal state-space map from the output signals whereby receipt of the particular substance by the biolayers of the biosensor devices can be detected.

Each transducer may be an interdigitated transducer. The biolayer of each biosensor device may be located on an interdigital transducer.

Each transducer may also include a first reflector array mounted on the piezoelectric material to receive the acoustic wave and reflect the acoustic wave back to the input transducer, and a second reflector array mounted on the piezoelectric material to receive the acoustic wave and reflect the acoustic wave back to the output transducer. The biolayer of each biosensor device may be located on a reflector array.

The biolayer of each biosensor device may be located on a portion of the piezoelectric material other than on a transducer or a reflector array.

The biolayer of each biosensor device may comprise an antibody different from an antibody of the biolayer of the other biosensor device. The antibodies may be orthogonal or semi-orthogonal to each other.

According to another aspect of the invention, a method of detecting a particular substance using a biosensor detection system includes providing at least two biosensor devices, each biosensor device including a piezoelectric material, an input transducer mounted on the piezoelectric material to receive an input radio frequency signal and propagate a corresponding acoustic wave within the piezoelectric material, an output transducer mounted on the piezoelectric material to receive the surface acoustic wave and transmit a corresponding output radio frequency signal, a biolayer mounted on the piezoelectric material to receive a substance to be tested and cause a corresponding change in the acoustic wave, and an oscillator circuit connected to the input transducer and to the output transducer, said oscillator circuit including an amplifier and producing an output signal indicative of a change in the acoustic wave, the biosensor devices having different biolayers, supplying a substance to be tested to the biolayers of the biosensor devices, and utilizing the output signals from the biosensor devices to detect receipt of the particular substance by the biolayers of the biosensor devices.

The method may include producing a signal state-space map from the output signals to enable receipt of a particular substance by the biolayers of the biosensor devices to be detected.

According to a still further aspect of the invention, a method of detecting and characterizing a particular substance using a biosensor detection system includes providing a system with at least two sensor devices, each sensor device including an X channel detector for detecting substance X and producing an X channel output signal proportional to the amount of substance X present and a Y channel detector for detecting substance Y and producing a Y channel output signal proportional to the amount of substance Y present, channel detectors X and Y comprising analogous chemical or biological groups operable to recognize similar structural analogs within substances Y and X, and substances X and Y comprising analogous chemical or biological groups operable to recognize similar structural analogs within channel detectors Y and X, and supplying a substance to be tested to the channel detectors and utilizing the output signals from the channel detectors to identify receipt by the channel detectors of the substance.

The method may include producing a signal state-space map from the output signals.

DESCRIPTION OF DRAWINGS

Embodiments of the invention will now be described by way of example, with reference to the accompanying drawings, of which.

DESCRIPTION OF PREFERRED EMBODIMENT

This invention provides a method of differentiating, identifying and characterizing structurally analogous chemical or biological substances with acoustic wave biosensors by using simple circuitry and mapping the multiple output signals of the circuitry on a signal state-space diagram. Such diagrams have previously been used in the digital communication field to map binary information onto magnitude-phase (phasor) plots commonly referred to as constellation diagrams.

Digital communication receivers selectively detect various groups of communication signals. These groups can be regionalized depending on their chosen method of modulation. Various modulation differences include, but are not limited to, frequency shift keying (FSK), phase shift keying (PSK), amplitude shift keying (ASK), and a combination of PSK and ASK such as quadrature amplitude modulation (QAM). A digital receiver can also differentiate between frequency-based modulation signaling such as frequency division multiple access (FDMA), or time-based modulation signaling such as time division multiple access (TDMA) systems.

Figure 1:
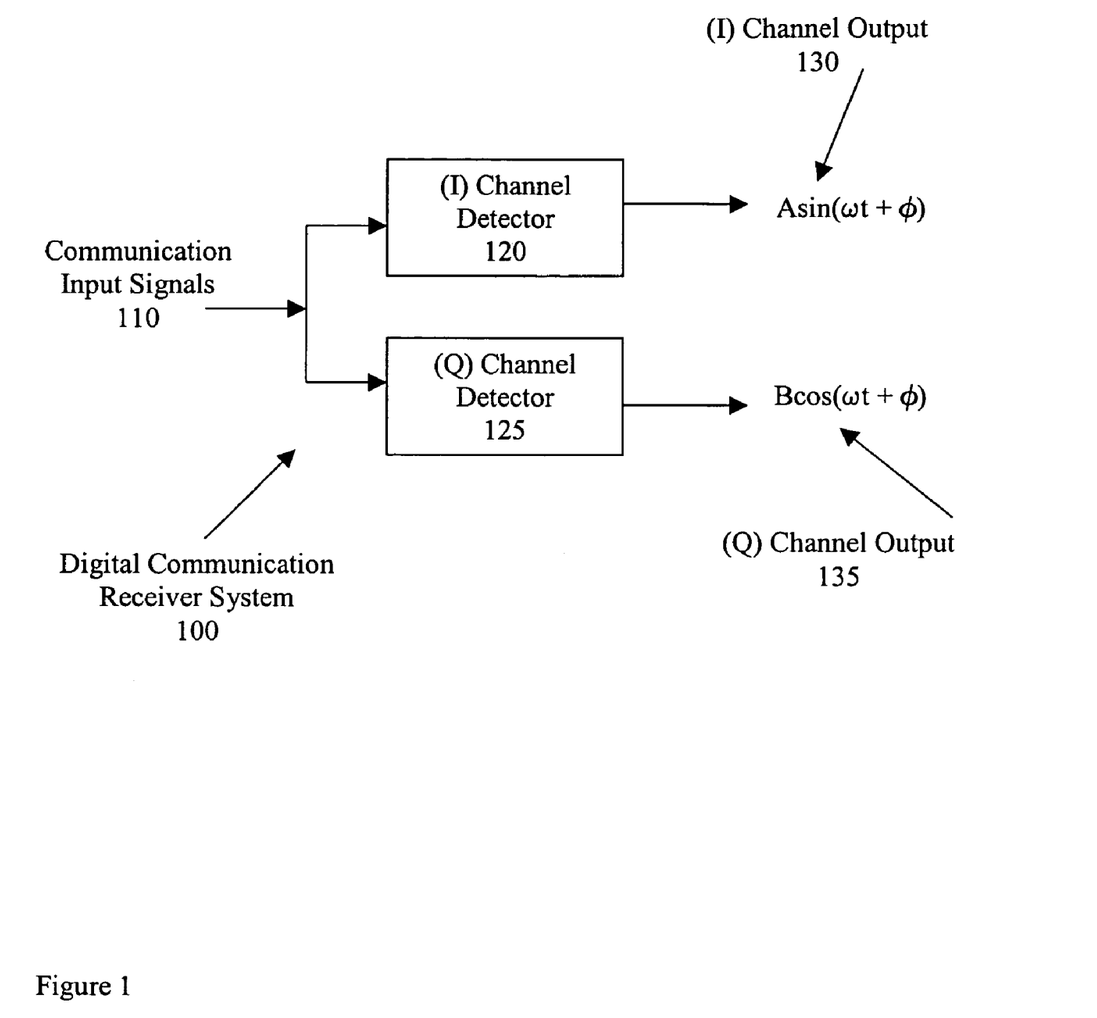
FIG. 1 is a diagrammatic view of a typical digital communication receiver system.

A typical digital communication receiver system 100 is illustrated in FIG. 1. A communication input signal 110 which may contain a multitude of modulation schemes, such as but not limited to ASK, FSK, PSK, FDMA or TDMA, is presented to the digital communication receiver system 100. The specific artificial intelligence embedded within the hardware and software of the digital communication receiver system 100 differentiates and identifies the desired group of signals using an in-phase (I) channel detector 120 and a quadrature-phase (Q) channel detector 125. The (I) channel output 130 has a signal comparable to A sin(ωt+φ) and the (Q) channel output 135 would have a signal comparable to B cos(ωt+φ). These two orthogonal outputs are then used as the values mapped to the coordinates of a magnitude-phase constellation plot.

Figure 2:
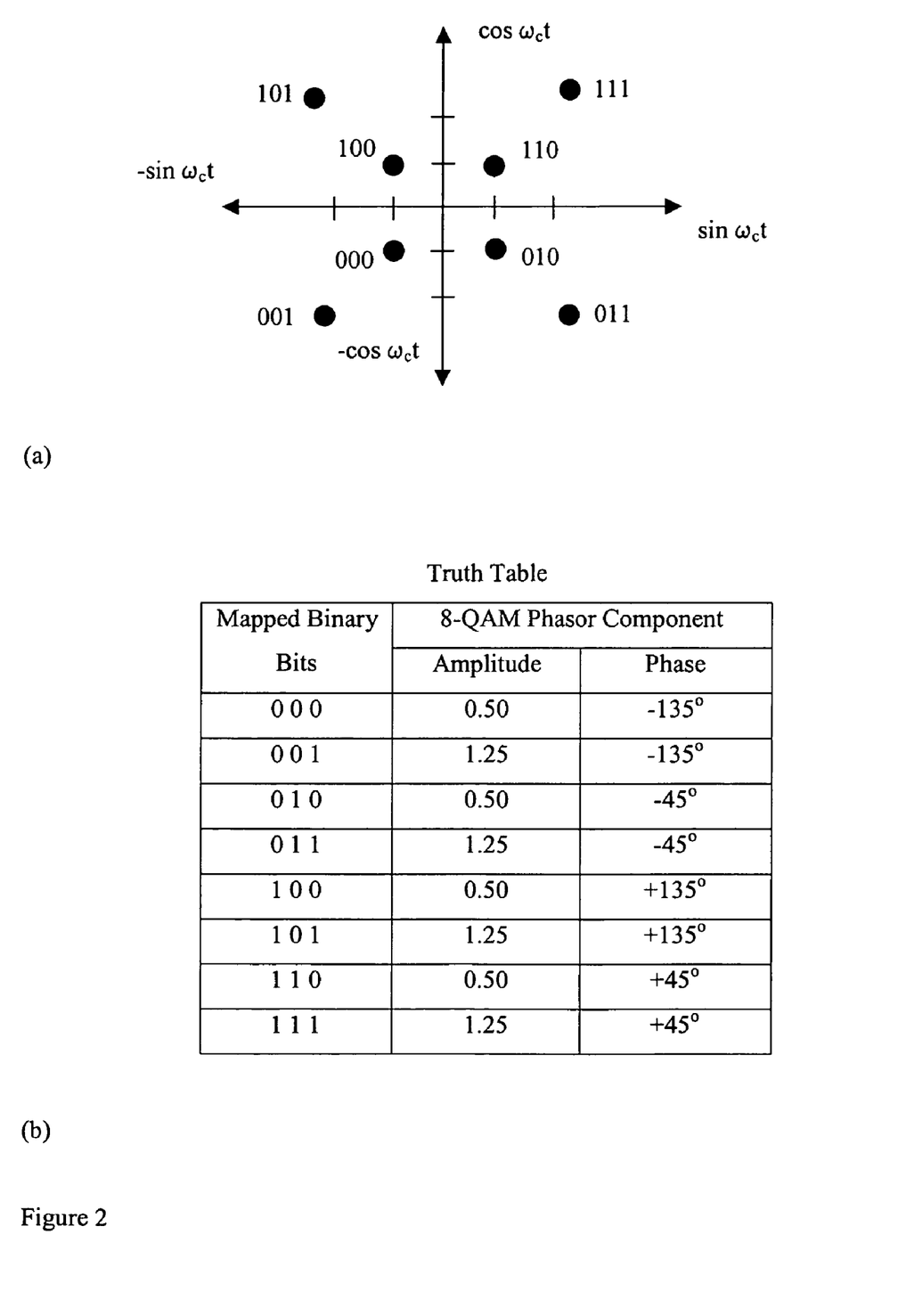
FIG. 2(a) shows a digital communication constellation diagram.
FIG. 2(b) shows a truth table for an 8-QAM communication detection system.

FIG. 2(a) shows a complex constellation diagram of an 8-level quadrature amplitude M-ary (8-QAM) encoding scheme. The digital information is contained in the amplitude (A), frequency (ω) and phase (φ) of the detected signals, with only the peak values being shown as filled-in circles. Such mapping of the binary information for an 8-QAM system is displayed in the truth table shown in FIG. 2(b). Within each row of the truth table, there is binary data identified by a magnitude and phase component of a constellation diagram.

The truth table is the result of the digital communication receiver system 100 being able to differentiate between a plurality of input signals 110, separate out the desired signals into (I) and (Q) channels, map and identify a binary sequence onto a constellation diagram.

Biosensors as reported by W. D. Hunt et al. "Time-dependent signatures of acoustic wave biosensors," *IEEE Proceedings*, Vol. 91, no: 6, pp. 890-901, June 2003 and Stubbs, D. D. et al "Investigation of cocaine plumes using surface acoustic wave immunoassay sensors," *Analytical Chemistry*, vol. 75, no. 22, pp. 6231-6235, Nov. 15, 2003 and Sang-Hun Lee et al "Real-Time Detection of Bacteria Spores Using a QCM Based Immunosensor," *Proceedings IEEE Sensor Symposium*, 2003 have been successfully assembled by immobilizing a monolayer of antibodies onto the surface of a surface acoustic wave (SAW) device.

Figure 3:
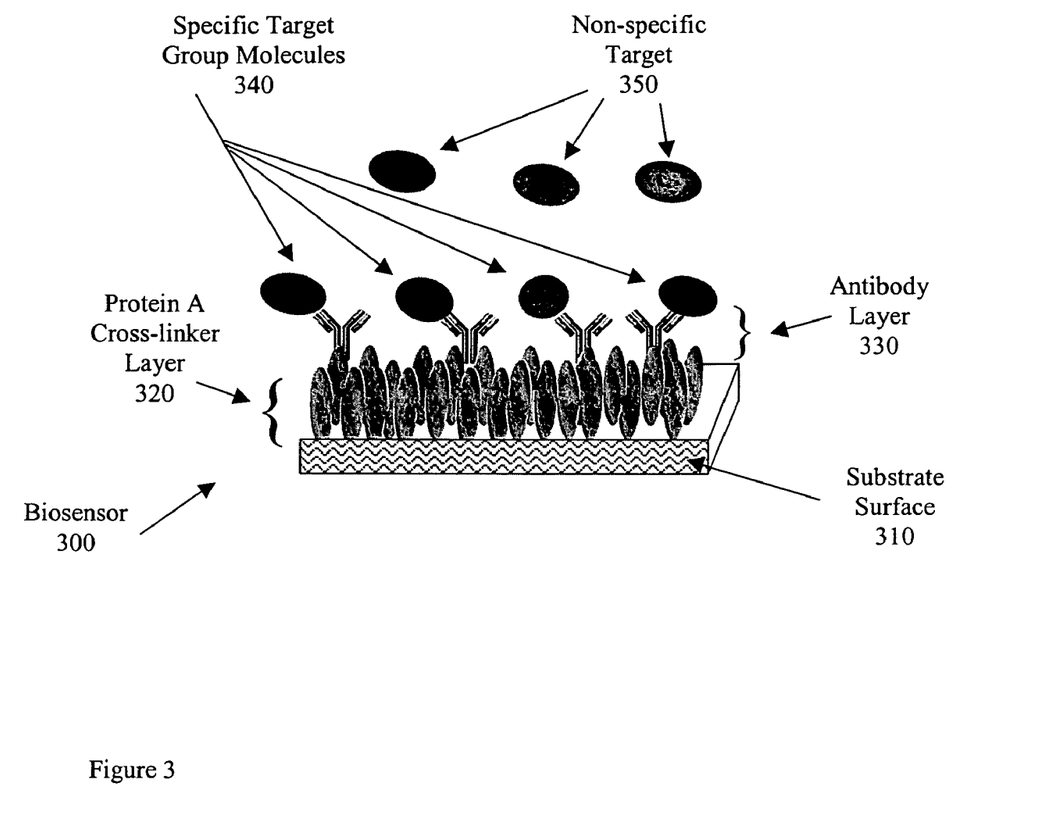
FIG. 3 shows the biological layers and other components of a biosensor.

The biological layers and components of such of a biosensor 300 are illustrated in FIG. 3. The biological layers are attached to the surface of a suitable acoustic wave substrate 310 such that a Protein A cross-linker layer 320 assists in interfacing with the antibody layer 330 and the substrate surface 310. The acoustic wave substrate may be any one of a variety of other acoustic wave substrates including but not limited to Surface Transverse Wave, Flexural Plate Wave, Bulk Acoustic Wave and Plate mode. A specific target group of molecules 340 will bind with the appropriate antibody layer 330 and will alter the mass and stiffness characteristics of the cross-linker layer 320 and antibody layer 330. A non-specific target group of molecules 350 will not bind with the appropriate antibody layer 330 and will not alter the mass and stiffness characteristics of the cross-link layer 320 and antibody layer 330. The biological layers comprising of the Protein A cross-linker layer 320 and the antibody layer 330 can be grouped as a receptor molecule layer where a receptor molecule layer may also include but not limited to DNA aptamers, a peptide or RNA aptamers. This change in mass and stiffness of the antibody biolayers 330 will affect the characteristics of the substrate 310 so that the acoustic wave which propagates within the substrate 310 is subjected to a modification of its acoustic velocity. This change in velocity transcribes into a frequency change as shown in the Sauerbrey equation (1), $$\Delta f = -\frac{2f_o^2 \rho_s}{V_a \rho_r} \quad (1)$$

Where
$\Delta f$=resonator frequency shift
$f_0$=resonator center frequency
$\rho_s$=mass density per m$^2$ of the layer attached to the device surface
$V_a$=acoustic wave velocity in the resonator
$\rho_r$=volume mass density of resonator material The elastic stiffness coefficient and mass density are perturbed by the antibody-antigen interaction resulting in a change of velocity, which therefore changes the resonant frequency of the SAW device. A more extensive version of this equation was derived and presented in W. D. Hunt et al ("Time-dependent signatures of acoustic wave biosensors," *IEEE Proceedings*, Vol. 91, no. 6, pp. 890-901, June 2003.) A simplified version of the integro-differential equation provided in the paper is presented in equation (2)

$$\Delta f(t) = -\frac{2f_o^2 \left( \Delta \rho_s(t) - \frac{\Delta \mu(t)}{V_s^2} \right)}{V_a \rho_r} \quad (2)$$

where $\Delta \mu(t)$ and $V_s$ are the stiffness parameters of the biolayer, attributes not included in the Sauerbrey equation. Another important aspect of this presentation is that it allows for the prospect of time varying mass and stiffness changes. Mathematically, this opens up the possibility of a SAW sensor frequency signature related to conformational changes in the immobilized biomolecular layer. In addition, much of the same approach would apply to multiple receptor/sensor configurations such as the micro-electromechanical systems (MEMS), nano-electromechanical systems (NEMS) or other mechanical resonator structures. Bulk Acoustic Wave substrates, and all of the types, can be configured such that the piezoelectric nature of the material is achieved by virtue of a thin film of piezoelectric material such as ZnO or AlN deposited on a substrate surface.

Figure 4:
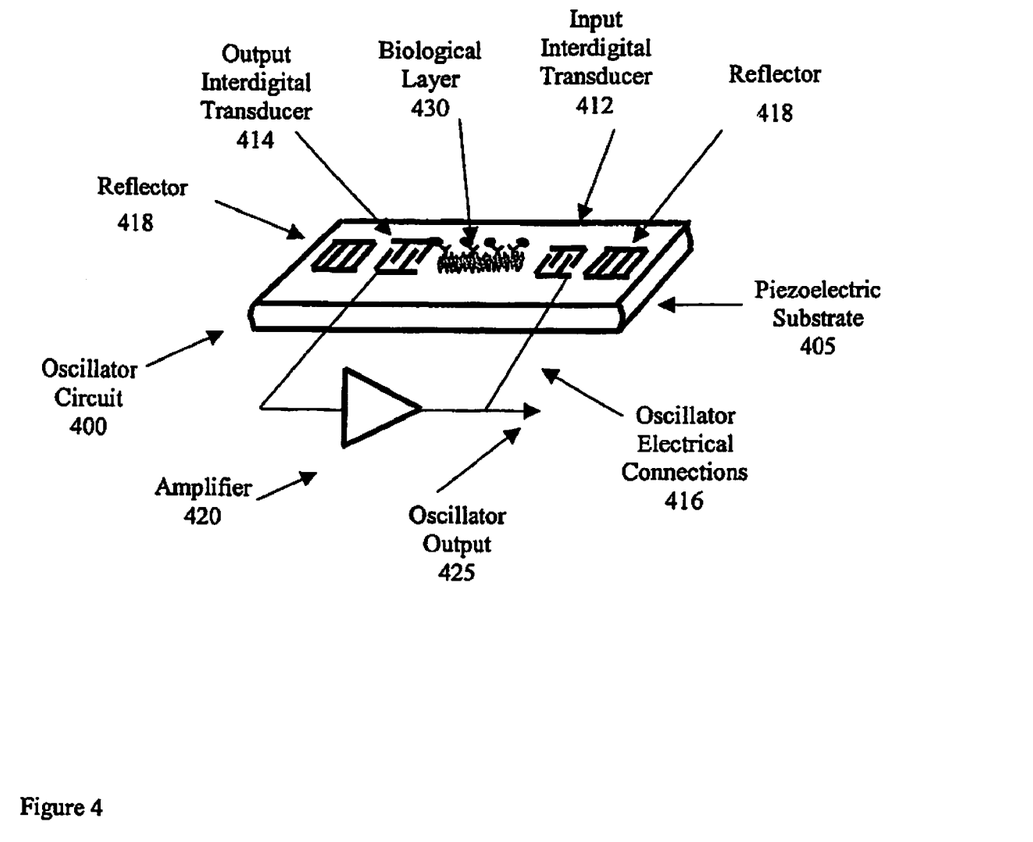
FIG. 4 shows the biosensor as a feedback element of an oscillator circuit.

FIG. 4 shows the biological layers and other components of a biosensor 300 used as the feedback element within an oscillator circuit 400. A piezoelectric substrate 405 has attached onto its surface an input interdigital transducer IDT 412 and an output IDT 414. The purpose of the IDTs is to both launch and receive the acoustic waves and to provide an electrical interface for external electrical connections 416. Reflectors 418 positioned beyond the IDTs 412 and 414 reflect the acoustic waves back into the IDT structures 412 and 414. This combination of IDTs 412, 414 and reflectors 418 produces an acoustic wave resonator configuration. Electrical connections 416 are connected to both the input and output of an amplifier 420. The amplifier 420 is shown for simplicity to be external to the substrate 405 but it can also reside on the substrate 405 with suitable electrical connections and fastening mechanisms between the amplifier 420 and the substrate itself.

The electrical output 425 of the oscillator will correspond to the frequency $f_0$ shown previously in equation (1), allowing the frequency changes to be precisely measured by external circuitry. The biolayers 430 are depicted as placed between the input IDT 412 and output IDT 414 but can be placed strategically throughout the area of the substrate 405. Hunt et al. have experimentally shown that the oscillator output electrical signal 425 can vary depending on whether the biolayer 430 is placed over IDT regions, reflector regions of a resonator structure or non-metallized regions and selective binding to the antibodies occurs.

Figure 5:
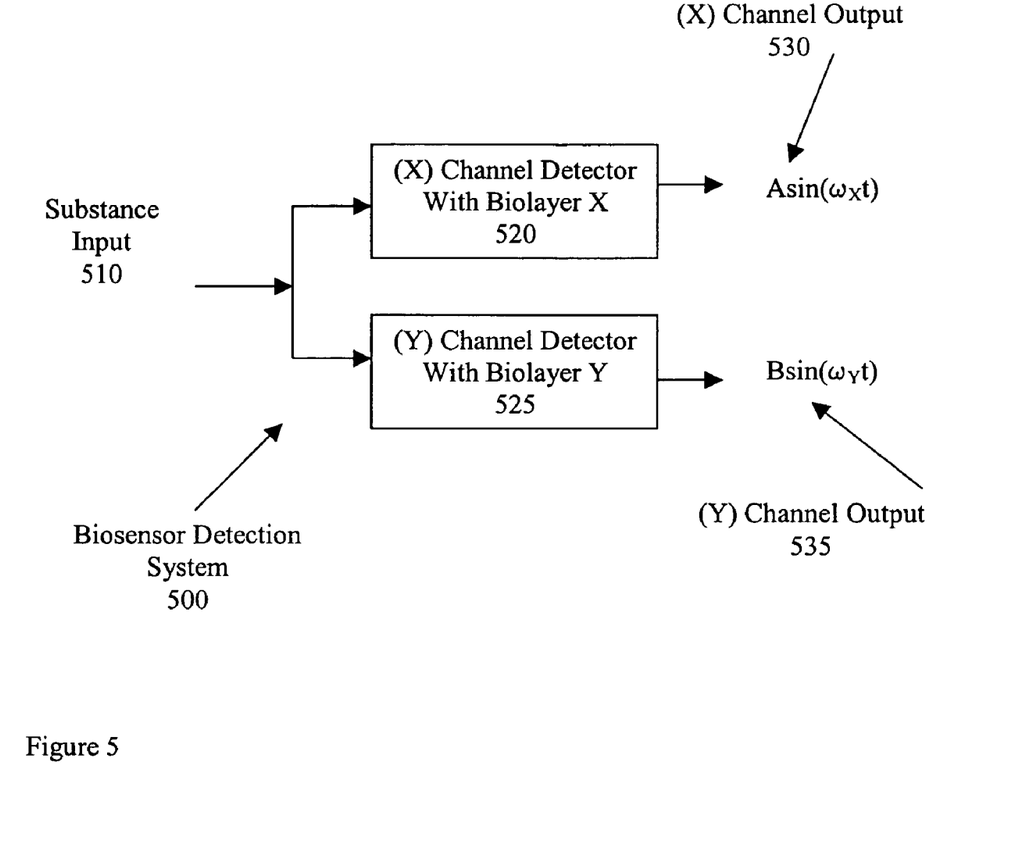
FIG. 5 shows a two-dimensional biosensor detection circuit in accordance with one embodiment of the invention.

A two-dimensional biosensor detection system 500 in accordance with the invention is shown in FIG. 5. An input substance 510 is presented to the system 500. The input substance 510 is presented to both the X channel detector 520 and Y channel detector 525. The X channel detector 520 has a biolayer with X-type antibodies and the Y channel detector 525 has a biolayer with Y-type antibodies. The X-channel output 530 signal A $\sin(\omega_X t)$ would depend on the binding action between the input substance 510 and antibody X within the X channel detector 520. The Y-channel output 535 signal B $\sin(\omega_Y t)$ would depend on the binding action between the input substance 510 and antibody Y within the Y channel detector 525.

The ability of antibody X within the X detector 520 to cross react with multiple antigens is known as the promiscuity of the antibody. This conformational diversity allows related groups of substances to bind with the antibody. The ability of an antibody to recognize multiple epitopes allows for the binding of analogous chemical or biological groups. The binding of structural analogs evolves from variations in conformational heterogeneity of the combining site, which controls both the affinity and specificity of the site (Venkatasamy Manivel, Naresh C. Sahoo, Dinakar M. Salunke, and Kanury V. S. Rao "Maturation of an Antibody Response Is Governed by Modulations in Flexibility of the Antigen-Combining Site," Immunity, Vol. 13, 611-620, November, 2000).

EXAMPLE

Figure 6:
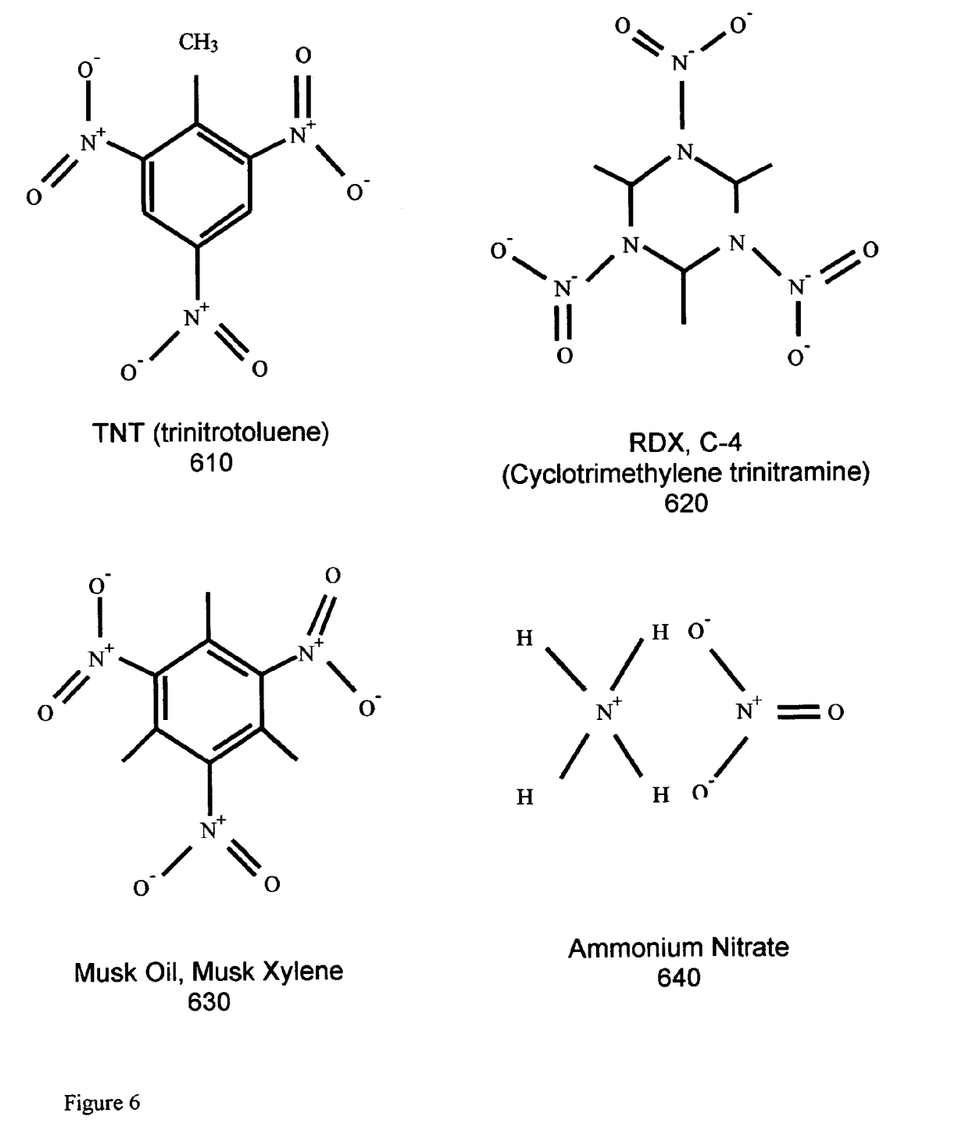
FIG. 6 shows the formulae of analogous groups of $NO_2$ based substances.

An example of a group of explosive substances presented to a biosenor in accordance with the invention will now be described. The substances in this example are related via an $NO_2$ branch and their formulae are shown in FIG. 6. Experiments conducted by Hunt et al. have shown that substances such as Trinitrotoluene (TNT) 610, Cyclotrimethylenetrinitramine (RDX) 620, Musk Oil or Musk Xylene 630 and ammonium nitrate (AN) 640 all bind differently with respect to TNT antibodies and RDX antibodies. A two-dimensional biosensor detection system 500 as shown in FIG. 5 was constructed. Input substances were presented separately to the system 500 at various distances and configurations from the biosensor input sampling head. A pneumatic system drew the input substances through an unheated filter into the detector system 500. The X channel detector 520 utilized the TNT antibody layer and the Y channel detector 525 utilized the RDX antibody layer. The frequency components of the X-channel output 530 signal A $\sin(\omega_X t)$ and the frequency component of the Y-channel output 535 signal B $\sin(\omega_Y t)$ were stored.

Figure 7:
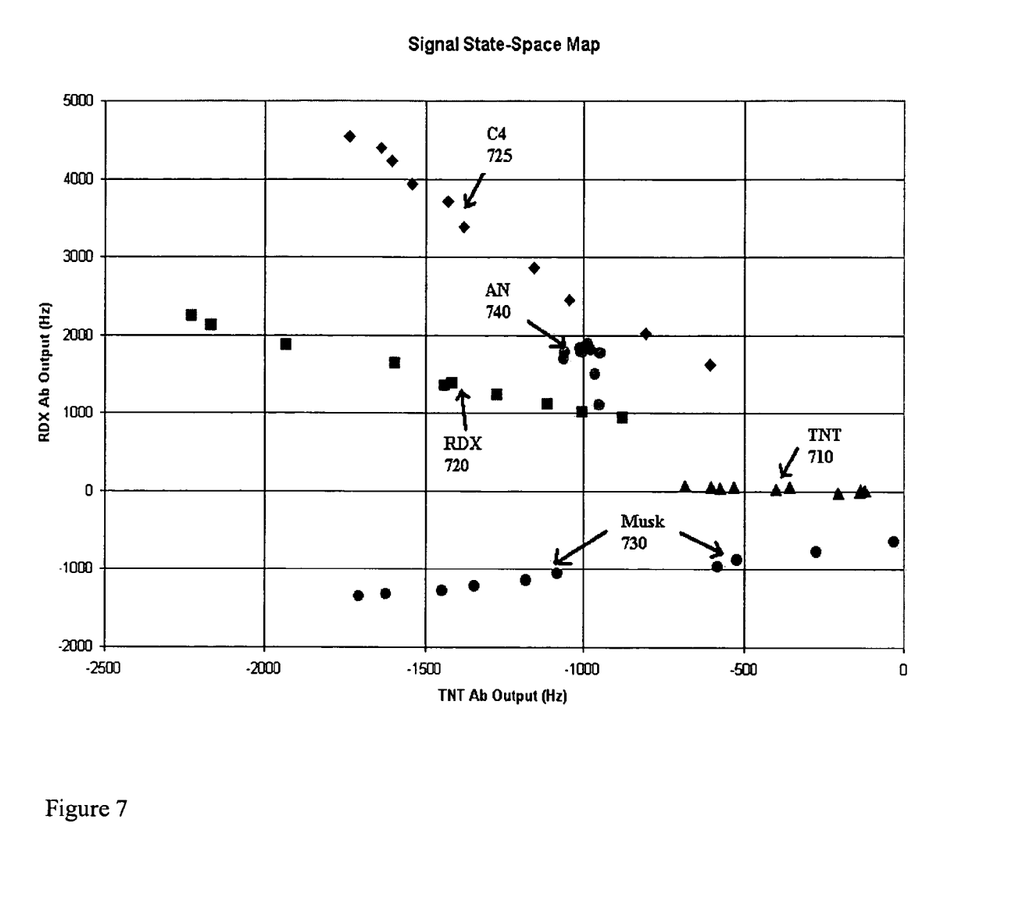
FIG. 7 shows a signal state-space map of analogous substances derived from information provided by the circuit of FIG. 5.

A signal state-space map was constructed and is shown in FIG. 7. The x-axis is comprised of the frequency component of the X-channel output 530 signal A $\sin(\omega_X t)$ and the y-axis is comprised of the frequency component of the Y-channel output 535 signal B $\sin(\omega_Y t)$. It is clearly shown that each substance is distinctively mapped in a region of the signal state-space map. This was achieved with a minimum of calculation and with no matrix or intricate mathematical computation.

The signal state-space map of FIG. 7 illustrates the grouping or clustering of substance data. The TNT 710 data occupies a region along the x-axis (−100 Hz to −700 Hz) and was derived from an INEEL vapour generator, with a flow of 150 cc/min at 13.2° C. and releasing 50 pg of TNT per pulse with a pulse duration of 0.3 seconds. The RDX data 720 occupies a region within the $2^{nd}$ quadrant (−1000, 1000) Hz to (−2250, 2200) Hz and was derived from an INEEL vapour generator with a flow of 150 cc/min at 53° C. releasing 50.3 pg of RDX per pulse with a pulse duration of 3.2 seconds. The C4 substance 725 data occupies a region within the $2^{nd}$ quadrant (−600, 1600) to (−1750, 4600) and was derived in an open lab with the filtered sampling head positioned 2 inches from material which was located at the bottom of a sample bottle. The Musk Oil data 730 occupies a region within the $3^{rd}$ quadrant (−10, −700) Hz to (−1700, −1300) Hz and was derived in the same open lab with a filtered sampling head positioned 3.5 inches from substance placed on a tray. The ammonium nitrate data 740 occupies a tight region within the $2^{nd}$ quadrant clustered around the coordinate (−1000, 1850) Hz and was also derived in an open lab with a filtered sampling head positioned 3.5 inches from the substance placed on a tray. In all cases, other than the INEEL generator sources, an unheated, 5 micron input filter was used.

The grouping or clustering of the substance data within the signal state-space map of FIG. 7 follows a logical pattern when the formulae of substances shown in FIG. 6 are considered. The similarity of the TNT and Musk substances are evident as the TNT is positioned only on the x-axis and the Musk is positioned in the $3^{rd}$ quadrant but extending in magnitude due to the higher vapour pressure of the Musk. The difference in magnitude between analogous substances can also be determined from the signal state-space map of FIG. 7. The C4 substance 725 was a larger sample (>1 gram) when compared to the RDX substance 720, which contained 50.3 pg per pulse with a pulse duration of 3.2 seconds. This is illustrated in FIG. 7 by the C4 data 725 having higher coordinate values compared to the RDX 720.

The semi-orthogonal relationship between the pairwise TNT and RDX antibodies is also evident in FIG. 7. For these specific antibodies whose data is shown in FIG. 7, the TNT 710 substance does not cross-react with the RDX antibody and can be considered to be truly orthogonal with respect thereto. However, the RDX 720 substance does cross-react to a certain degree with the TNT antibody and a semi-orthogonal relationship is present. The substances containing C4 725, Musk 730 and AN 740 all cross-react to some degree with both the TNT and RDX antibodies.

It should also be recognized that the signal state-space map of FIG. 7 only contains ten samples of each substance. These samples were acquired during the transient stage of the pneumatic system. Even with this short accumulation of data, clear and defined regions appear on the map which involved a very low computational effort. The sampling rate can range from milli-seconds to tens or hundreds of seconds depending on the application.

Figure 8:
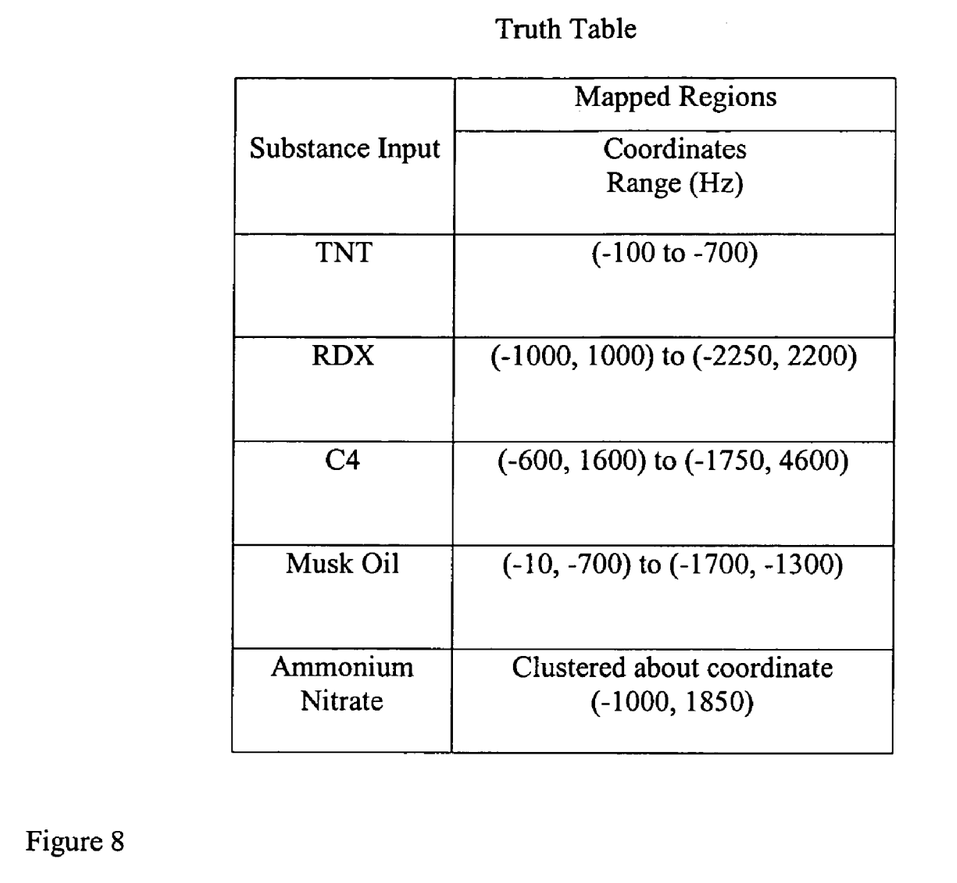
FIG. 8 shows an equivalent truth table for a substance detection system.

This mapping of the substance information for the data shown in FIG. 7 is displayed in a truth table shown in FIG. 8. Within each row of the truth table, there is a substance identified by a magnitude and phase, shown in an (x,y) coordinate system of the components of the signal state-space map of FIG. 7. This truth table of FIG. 8 would in fact perform as a look up table within an algorithm to quickly differentiate and identify a sampled substance.

Figure 9:
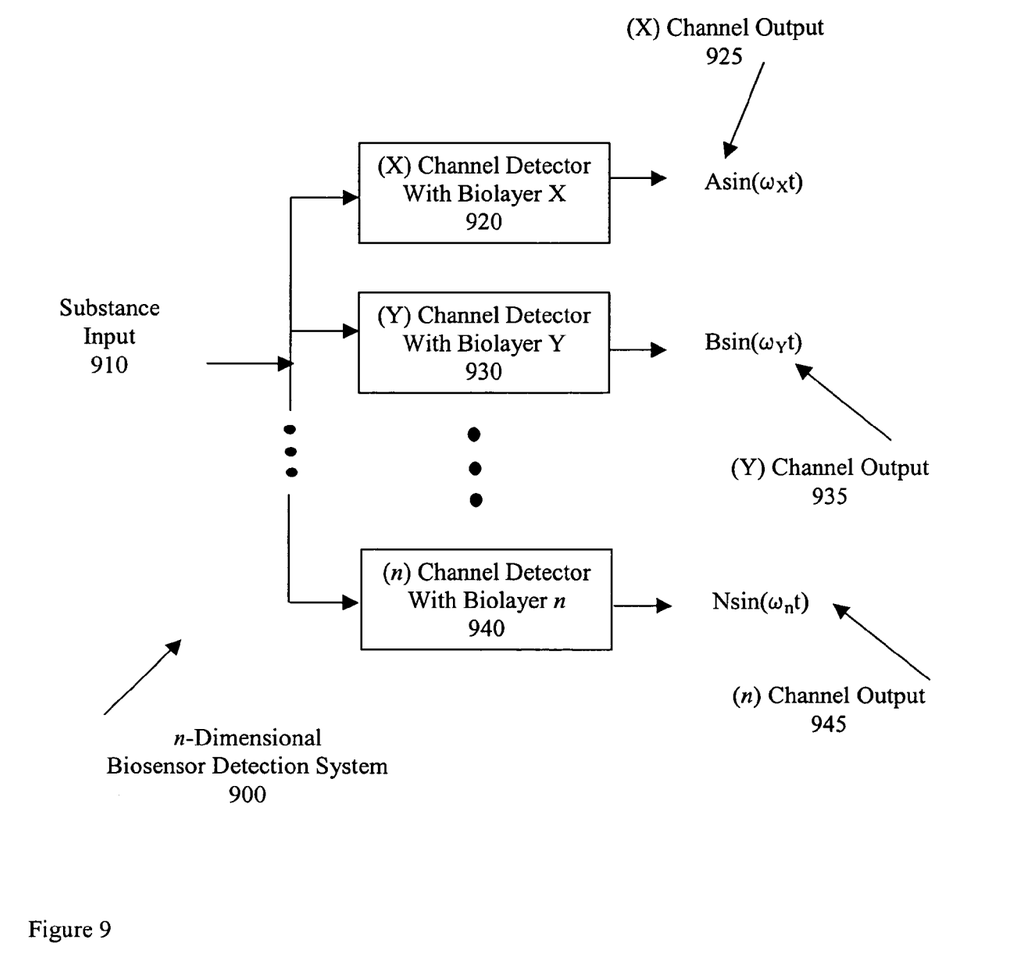
FIG. 9 shows an $n^{th}$-dimensional biosensor detection circuit in accordance with a further embodiment of the invention.

This method to differentiate, identify and characterize structurally analogous chemical or biological substances based on orthogonal signal state-space mapping can also be extended to a three-dimensional map or, in the limits, to an n-dimensional map. The two-dimensional biosensor detection system 500 shown in FIG. 5 can be extended to an n-dimensional detection system 900 shown in FIG. 9. An input substance 910 is presented to the system 900. This input substance 910 is presented to all of the X 920, Y 930 and n 940 channel detectors. The X channel detector 920 has a biolayer with X-type antibodies and, in continuation, the $n^{th}$ channel detector 940 has a biolayer with n-type antibodies. The $n^{th}$-channel output 945 signal N $\sin(\omega_n t)$ will depend on the binding action between the input substance 910 and antibody n within the $n^{th}$ channel detector 940.

This method to differentiate and identify analogous chemical or biological substances based on semi-orthogonal signal state-space mapping is well suited for low-cost low-powered handheld or remote detection units within the environmental, agricultural, medical and security concerns. The simple mapping technique can be applied to all forms of detection schemes where a signal state-space diagram can be generated that identify the distinct regions of analogous chemical or biological substances. The substances to be detected could range from mold spores, *E-coli*(*Escherichia coli* O157:H7), harmful pathogens, drugs and explosives. Such substances could be in vapour, liquid or solid form.

The advantages of the invention will now be readily apparent to a person skilled in the art from the above description of preferred embodiments. Other embodiments and advantages of the invention will also now be readily apparent to a person skilled in the art, the scope of the invention being defined in the appended claims.

The invention claimed is:

1. A biosensor detection system for detecting a particular substance, said system having:
at least two biosensor devices, each biosensor device including:
   a piezoelectric material,
   an input transducer mounted on the piezoelectric material to receive an input radio frequency signal and propagate a corresponding acoustic wave within the piezoelectric material,
   an output transducer mounted on the piezoelectric material to receive the acoustic wave and transmit a corresponding output radio frequency signal,
   a biolayer mounted on the piezoelectric material to receive a substance to be tested and cause a corresponding change in the acoustic wave, and
   an oscillator circuit connected to the input transducer and to the output transducer, said oscillator circuit including an amplifier and providing an output signal indicative of a change in the acoustic wave,
the biosensor devices having two different biolayers which are chemically orthogonal or semi-orthogonal to each other, whereby the output signals can be utilized to detect receipt of a particular substance by the biolayers of the biosensor devices.

2. A biosensor detection system according to claim 1 including a signal state-space map formulator operable to produce a signal state-space map from the output signals whereby receipt of the particular substance by the biolayers of the biosensor devices can be detected.

3. A biosensor detection system according to claim 1 wherein each transducer is an interdigitated transducer.

4. A biosensor detection system according to claim 3 wherein the biolayer of each biosensor device is located on an interdigital transducer.

5. A biosensor detection system according to claim 1 wherein each transducer also includes a first reflector array mounted on the piezoelectric material to receive the acoustic wave and reflect the acoustic wave back to the input transducer, and a second reflector array mounted on the piezoelectric material to receive the acoustic wave and reflect the acoustic wave back to the output transducer.

6. A biosensor detection system according to claim 5 wherein the biolayer of each biosensor device is located on a reflector array.

7. A biosensor detection system according to claim 1 wherein the biolayer of each biosensor device is located on a portion of the piezoelectric material other than on a transducer or a reflector array.

8. A biosensor detection system according to claim 1 wherein the biolayer of each biosensor device comprises an antibody which is chemically orthogonal or semi-orthogonal to an antibody of the biolayer of the other biosensor device.

9. A method of detecting a particular substance using a biosensor detection system, said method including:
providing at least two biosensor devices, each biosensor device including:
   a piezoelectric material,
   an input transducer mounted on the piezoelectric material to receive an input radio frequency signal and propagate a corresponding acoustic wave within the piezoelectric material,
   an output transducer mounted on the piezoelectric material to receive the surface acoustic wave and transmit a corresponding output radio frequency signal,
   a biolayer mounted on the piezoelectric material to receive a substance to be tested and cause a corresponding change in the acoustic wave, and
   an oscillator circuit connected to the input transducer and to the output transducer, said oscillator circuit including an amplifier and producing an output signal indicative of a change in the acoustic wave,
the biosensor devices having different biolayers which are chemically orthogonal or semi-orthogonal to each other,
supplying a substance to be tested to the biolayers of the biosensor devices, and
utilizing the output signals from the biosensor devices to detect receipt of the particular substance by the biolayers of the biosensor devices.

10. A method according to claim 9 including producing a signal state-space map from the output signals to enable receipt of a particular substance by the biolayers of the biosensor devices to be detected.

* * * * *